(12) United States Patent
Hadley et al.

(10) Patent No.: US 11,565,089 B2
(45) Date of Patent: Jan. 31, 2023

(54) CATHETER INSERTION DEVICE INCLUDING RETRACTABLE NEEDLE

(71) Applicant: C. R. Bard, Inc., Franklin Lakes, NJ (US)

(72) Inventors: Chad A. Hadley, North Salt Lake, UT (US); Jacob B. Braithwaite, Sandy, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/337,273

(22) Filed: Jun. 2, 2021

(65) Prior Publication Data

US 2021/0283379 A1    Sep. 16, 2021

Related U.S. Application Data

(63) Continuation of application No. 16/295,906, filed on Mar. 7, 2019, now Pat. No. 11,033,719, which is a
(Continued)

(51) Int. Cl.
*A61M 25/06* (2006.01)

(52) U.S. Cl.
CPC ..... *A61M 25/0631* (2013.01); *A61M 25/0606* (2013.01)

(58) Field of Classification Search
CPC ..................... A61M 25/0631; A61M 25/0606
See application file for complete search history.

(56) References Cited

U.S. PATENT DOCUMENTS

| 2,211,975 A | 8/1940 | Hendrickson |
| 2,259,488 A | 10/1941 | Raiche |

(Continued)

FOREIGN PATENT DOCUMENTS

| AU | 691141 B2 | 5/1998 |
| AU | 710967 B2 | 9/1999 |

(Continued)

OTHER PUBLICATIONS

EP 22159383.3 filed Mar. 1, 2022 Extended European Search Report dated May 30, 2022.

(Continued)

*Primary Examiner* — Tasnim Mehjabin Ahmed
(74) *Attorney, Agent, or Firm* — Rutan & Tucker LLP

(57) ABSTRACT

A catheter insertion device for inserting a catheter into a body of a patient is disclosed. The catheter insertion device includes a retractable needle for establishing access to a subcutaneous vessel of the patient and a manually extensible guidewire for guiding the initially attached catheter into the vessel. In one embodiment, the catheter insertion device comprises a housing, a hollow needle retractably extending from the housing, a catheter initially disposed on a portion of the needle, a guidewire including a portion initially disposed within the needle, a guidewire advancement feature configured to selectively advance a distal end of the guidewire distally past a distal end of the needle, and a needle retention component configured to selectively enable retraction of the needle into the housing. The needle retention component is configured to be actuated by the guidewire advancement feature. In one embodiment, one-handed operation of the device is possible.

6 Claims, 13 Drawing Sheets

Related U.S. Application Data continuation of application No. 14/846,387, filed on Sep. 4, 2015, now Pat. No. 10,232,146.

(60) Provisional application No. 62/046,722, filed on Sep. 5, 2014.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,766,916 A | 10/1973 | Moorehead et al. |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |

(56) References Cited

U.S. PATENT DOCUMENTS

| | | |
|---|---|---|
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |

(56) References Cited

U.S. PATENT DOCUMENTS

| | | |
|---|---|---|
| 5,855,615 A | 1/1999 | Bley et al. |
| 5,858,002 A | 1/1999 | Jesch |
| 5,865,806 A * | 2/1999 | Howell ............ A61M 25/0693 |
| | | 604/164.12 |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,599,296 B1 | 7/2003 | Gillick et al. |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |

(56) References Cited

U.S. PATENT DOCUMENTS

| | | |
|---|---|---|
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |

(56) References Cited

U.S. PATENT DOCUMENTS

| | | |
|---|---|---|
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 3,029,470 A1 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,958 B2 | 1/2014 | Jones et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |

(56) References Cited

U.S. PATENT DOCUMENTS

| | | |
|---|---|---|
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 11,389,626 B2 | 7/2022 | Tran et al. |
| 11,400,260 B2 | 8/2022 | Huang et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0004532 A1 | 1/2005 | Woehr et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long |
| 2005/0273057 A1 | 12/2005 | Popov |
| 2006/0025721 A1 | 2/2006 | Duffy et al. |
| 2006/0036219 A1 | 2/2006 | Alvin |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |

(56) References Cited

U.S. PATENT DOCUMENTS

| | | |
|---|---|---|
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1* | 8/2010 | Belson ............ A61B 5/150503 600/371 |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0004162 A1 | 1/2011 | Tal |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1* | 8/2012 | Hall ............ A61M 25/0606 604/164.12 |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1 | 4/2015 | Schraga |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |

(56) References Cited

U.S. PATENT DOCUMENTS

| | | | |
|---|---|---|---|
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0089513 A1* | 3/2016 | Ishida ............... A61M 25/0631 |
| | | | 604/164.08 |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0052858 A1 | 2/2021 | Isaacson et al. |
| 2021/0308428 A1 | 10/2021 | Blanchard et al. |
| 2021/0402155 A1 | 12/2021 | Hall et al. |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 0730880 A1 | 9/1996 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 2150304 A2 | 2/2010 |
| EP | 2272432 A1 | 1/2011 |
| EP | 2569046 A1 | 3/2013 |
| GB | 2529270 A | 2/2016 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| JP | 6692869 B2 * | 5/2020 ........ A61M 25/0606 |
| WO | 83/01575 A1 | 5/1983 |
| WO | 1992013584 A1 | 8/1992 |
| WO | 92/22344 A1 | 12/1992 |
| WO | 1994006681 A2 | 3/1994 |
| WO | 1995011710 A1 | 5/1995 |
| WO | 95/19193 A1 | 7/1995 |
| WO | 95/23003 A1 | 8/1995 |
| WO | 96/32981 A1 | 10/1996 |
| WO | 1996040359 A1 | 12/1996 |
| WO | 97/05912 A2 | 2/1997 |
| WO | 97/21458 A1 | 6/1997 |
| WO | 1997045151 A1 | 12/1997 |
| WO | 98/24494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 00/67829 A1 | 11/2000 |
| WO | 2001007103 A1 | 2/2001 |
| WO | 01/26725 A1 | 4/2001 |
| WO | 02/41932 A2 | 5/2002 |
| WO | 02/066093 A2 | 8/2002 |
| WO | 03/11381 A1 | 2/2003 |
| WO | 03/043686 A1 | 5/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |

(56) References Cited

FOREIGN PATENT DOCUMENTS

| | | | |
|---|---|---|---|
| WO | 2008/131300 | A2 | 10/2008 |
| WO | 2008/137956 | A2 | 11/2008 |
| WO | 2009/001309 | A1 | 12/2008 |
| WO | 2008147600 | A1 | 12/2008 |
| WO | 2009031161 | A1 | 3/2009 |
| WO | 2009114837 | A2 | 9/2009 |
| WO | 2009/124990 | A1 | 10/2009 |
| WO | 2010015676 | A1 | 2/2010 |
| WO | 2010/048449 | A2 | 4/2010 |
| WO | 2010/132608 | A2 | 11/2010 |
| WO | 2011036574 | A1 | 3/2011 |
| WO | 2011/143621 | A1 | 11/2011 |
| WO | 2012106266 | A1 | 8/2012 |
| WO | 2012154277 | A1 | 11/2012 |
| WO | 2012166746 | A1 | 12/2012 |
| WO | 2012174109 | A1 | 12/2012 |
| WO | 2013119557 | A1 | 8/2013 |
| WO | 2013126446 | A1 | 8/2013 |
| WO | 2013187827 | A1 | 12/2013 |
| WO | 2014006403 | A1 | 1/2014 |
| WO | 2014029424 | A1 | 2/2014 |
| WO | 2014074417 | A2 | 5/2014 |
| WO | 2014081942 | A1 | 5/2014 |
| WO | 2014/123848 | A1 | 8/2014 |
| WO | 2014120741 | A1 | 8/2014 |
| WO | 2014133617 | A1 | 9/2014 |
| WO | 2014140257 | A1 | 9/2014 |
| WO | 2014140265 | A1 | 9/2014 |
| WO | 2014/165783 | A1 | 10/2014 |
| WO | 2014158908 | A1 | 10/2014 |
| WO | 2014182421 | A1 | 11/2014 |
| WO | 2014197656 | A1 | 12/2014 |
| WO | 2014204593 | A1 | 12/2014 |
| WO | 2015017136 | A1 | 2/2015 |
| WO | 2015024904 | A1 | 2/2015 |
| WO | 2015035393 | A1 | 3/2015 |
| WO | 2015058136 | A1 | 4/2015 |
| WO | 15108913 | A1 | 7/2015 |
| WO | 2015/168655 | A2 | 11/2015 |
| WO | 15164912 | A1 | 11/2015 |
| WO | 2016/037127 | A1 | 3/2016 |
| WO | 16178974 | A1 | 11/2016 |
| WO | 2018/049413 | A1 | 3/2018 |
| WO | 2018170349 | A1 | 9/2018 |
| WO | 2019173641 | A1 | 9/2019 |

OTHER PUBLICATIONS

PCT/US2019/052225 filed Sep. 20, 2019 International Search Report and Written Opinion dated Jun. 25, 2020.
U.S. Appl. No. 16/868,461, filed May 6, 2020 Final Office Action dated May 25, 2022.
U.S. Appl. No. 16/996,769, filed Aug. 18, 2020 Notice of Allowance dated Jun. 13, 2022.
U.S. Appl. No. 15/869,872, filed Jan. 12, 2018 Notice of Allowance dated Dec. 24, 2021.
U.S. Appl. No. 16/296,087, filed Mar. 7, 2019 Notice of Allowance dated Mar. 8, 2022.
U.S. Appl. No. 16/490,023, filed Aug. 29, 2019 Notice of Allowance dated Mar. 14, 2022.
U.S. Appl. No. 16/868,461, filed May 6, 2020 Non-Final Office Action dated Feb. 15, 2022.
U.S. Appl. No. 16/996,769, filed Aug. 18, 2020 Non-Final Office Action dated Mar. 2, 2022.
JP 2016-107046 filed May 30, 2016 Office Action dated Jul. 28, 2016.
JP 2016-107046 filed May 30, 2016 Office Action dated Nov. 7, 2017.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Landmark™ Aquavene® Catheters Brochure, 1992.
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PCT/US2019/021231 filed Mar. 7, 2019 International Search Report and Written Opinion, dated Jun. 27, 2019.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.

(56) References Cited

OTHER PUBLICATIONS

U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-lntima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797029.2 filed Nov. 21, 2017 Office Action dated Mar. 27, 2020.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
EP17849786.3 filed Apr. 12, 2019 Extended European Search Report dated May 13, 2020.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
U.S. Appl. No. 16/296,087, filed Mar. 7, 2019 Final Office Action dated Sep. 10, 2021.
U.S. Appl. No. 16/450,800, filed Jun. 24, 2019 Notice of Allowance dated Nov. 3, 2021.
U.S. Appl. No. 16/490,023, filed Aug. 29, 2019 Non-Final Office Action dated Oct. 4, 2021.
U.S. Appl. No. 16/529,622, filed Aug. 1, 2019 Notice of Allowance dated Aug. 23, 2021.
PCT/US2020/046860 filed Aug. 18, 2020 International Search Report and Written Opinion dated Nov. 18, 2020.
U.S. Appl. No. 16/696,844, filed Nov. 26, 2019 Non-Final Office Action dated Aug. 1, 2022.
U.S. Appl. No. 16/867,349, filed May 5, 2020 Non-Final Office Action dated Jun. 16, 2022.
U.S. Appl. No. 17/164,653, filed Feb. 1, 2021, Restriction Requirement dated Sep. 7, 2022.
U.S. Appl. No. 16/296,087, filed Mar. 7, 2019 Non-Final Office Action dated Mar. 26, 2021.
U.S. Appl. No. 16/296,087, filed Mar. 7, 2019 Restriction Requirement dated Feb. 8, 2021.
U.S. Appl. No. 16/389,719, filed Apr. 19, 2019 Final Office Action dated Jun. 14, 2021.
U.S. Appl. No. 16/389,719, filed Apr. 19, 2019 Non-Final Office Action dated Mar. 19, 2021.
U.S. Appl. No. 16/450,800, filed Jun. 24, 2019 Non-Final Office Action dated Jul. 9, 2021.
U.S. Appl. No. 16/490,023, filed Aug. 29, 2019 Restriction Requirement dated May 4, 2021.
U.S. Appl. No. 16/529,602, filed Aug. 1, 2019 Notice of Allowance dated Jan. 19, 2021.
U.S. Appl. No. 16/529,622, filed Aug. 1, 2019 Non-Final Office Action dated May 7, 2021.
U.S. Appl. No. 29/536,043, filed Aug. 12, 2015 Final Office Action dated Mar. 26, 2018.

(56) References Cited

OTHER PUBLICATIONS

U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
U.S. Appl. No. 29/654,521, filed Jun. 25, 2018 Notice of Allowability dated Sep. 30, 2020.
U.S. Appl. No. 29/654,521, filed Jun. 25, 2018 Notice of Allowance dated Aug. 17, 2020.
U.S. Appl. No. 29/654,521, filed Jun. 25, 2018 Restriction Requirement dated Apr. 8, 2020.
U.S. Appl. No. 29/654,527, filed Jun. 25, 2018 Notice of Allowability dated Sep. 30, 2020.
U.S. Appl. No. 29/654,527, filed Jun. 25, 2018 Notice of Allowance dated Aug. 18, 2020.
U.S. Appl. No. 29/654,527, filed Jun. 25, 2018 Restriction Requirement dated Mar. 10, 2020.
U.S. Appl. No. 29/658,136, filed Jul. 27, 2018 Non-Final Office Action dated Sep. 9, 2020.
U.S. Appl. No. 29/658,136, filed Jul. 27, 2018 Notice of Allowance dated Mar. 23, 2021.
U.S. Appl. No. 29/658,136, filed Jul. 27, 2018 Restriction Requirement dated May 11, 2020.
Waltimire, B. and Rasor, J.S., Midline catheter Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
U.S. Appl. No. 14/044,623, filed Oct. 2, 2013 Notice of Allowance dated Nov. 6, 2014.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Notice of Allowance dated Aug. 19, 2020.
U.S. Appl. No. 14/250,093, filed Apr. 10, 2014 Panel Decision dated Jul. 14, 2017.
U.S. Appl. No. 14/250,093, filed Apr. 10, 2014 Patent Board Decision dated Jun. 8, 2020.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Feb. 25, 2019.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/846,387, filed Sep. 4, 2015 Notice of Allowance dated Oct. 29, 2018.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Allowance dated Sep. 24, 2020.
U.S. Appl. No. 14/866,738, filed Sep. 25, 2015 Notice of Panel Decision dated Jun. 23, 2017.
U.S. Appl. No. 14/866,738, filed Sep. 25, 2015 Patent Board Decision dated Jul. 13, 2020.
U.S. Appl. No. 14/876,735, filed Oct. 6, 2015 Non-Final Office Action dated Mar. 30, 2017.
U.S. Appl. No. 15/154,384, filed May 13, 2016 Final Office Action dated Dec. 24, 2020.

(56) References Cited

OTHER PUBLICATIONS

U.S. Appl. No. 15/154,384, filed May 13, 2016 Final Office Action dated Nov. 27, 2019.
U.S. Appl. No. 15/154,384, filed May 13, 2016 Non-Final Office Action dated Jun. 26, 2020.
U.S. Appl. No. 15/154,384, filed May 13, 2016 Non-Final Office Action dated Jun. 28, 2019.
U.S. Appl. No. 15/154,384, filed May 13, 2016 Notice of Allowance dated Apr. 29, 2021.
U.S. Appl. No. 15/154,384, filed May 13, 2016 Notice of Allowance dated Mar. 17, 2021.
U.S. Appl. No. 15/154,384, filed May 13, 2016 Restriction Requirment dated Jan. 25, 2019.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.
U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Final Office Action dated Jan. 28, 2020.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/727,528, filed Oct. 6, 2017 Notice of Allowance dated Mar. 27, 2020.
U.S. Appl. No. 15/862,380, filed Jan. 4, 2018 Final Office Action dated Oct. 26, 2020.
U.S. Appl. No. 15/862,380, filed Jan. 4, 2018 Non-Final Office Action dated Jul. 9, 2020.
U.S. Appl. No. 15/862,380, filed Jan. 4, 2018 Notice of Allowance dated Jun. 16, 2021.
U.S. Appl. No. 15/862,380, filed Jan. 4, 2018 Restriction Requirement dated Dec. 23, 2019.
U.S. Appl. No. 15/869,872, filed Jan. 12, 2018 Advisory Action dated Sep. 23, 2020.
U.S. Appl. No. 15/869,872, filed Jan. 12, 2018 Final Office Action dated Jun. 25, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Non-Final Office Action dated Nov. 4, 2019.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 16/292,076, filed Mar. 4, 2019 Corrected Notice of Allowance dated Feb. 25, 2021.
U.S. Appl. No. 16/292,076, filed Mar. 4, 2019 Non-Final Office Action dated Aug. 10, 2020.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/295,906, filed Mar. 7, 2019 Non-Final Office Action dated Sep. 4, 2020.
U.S. Appl. No. 16/295,906, filed Mar. 7, 2019 Notice of Allowance dated Mar. 4, 2021.

* cited by examiner

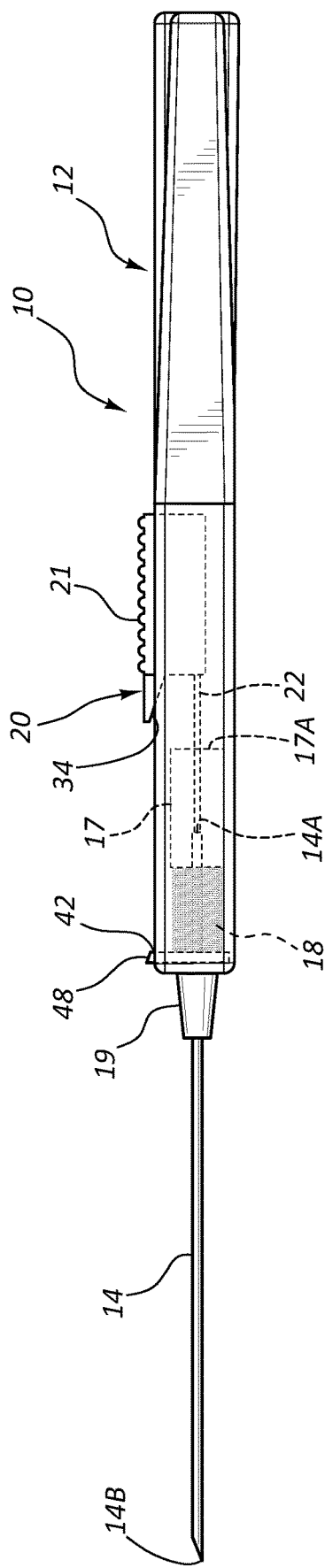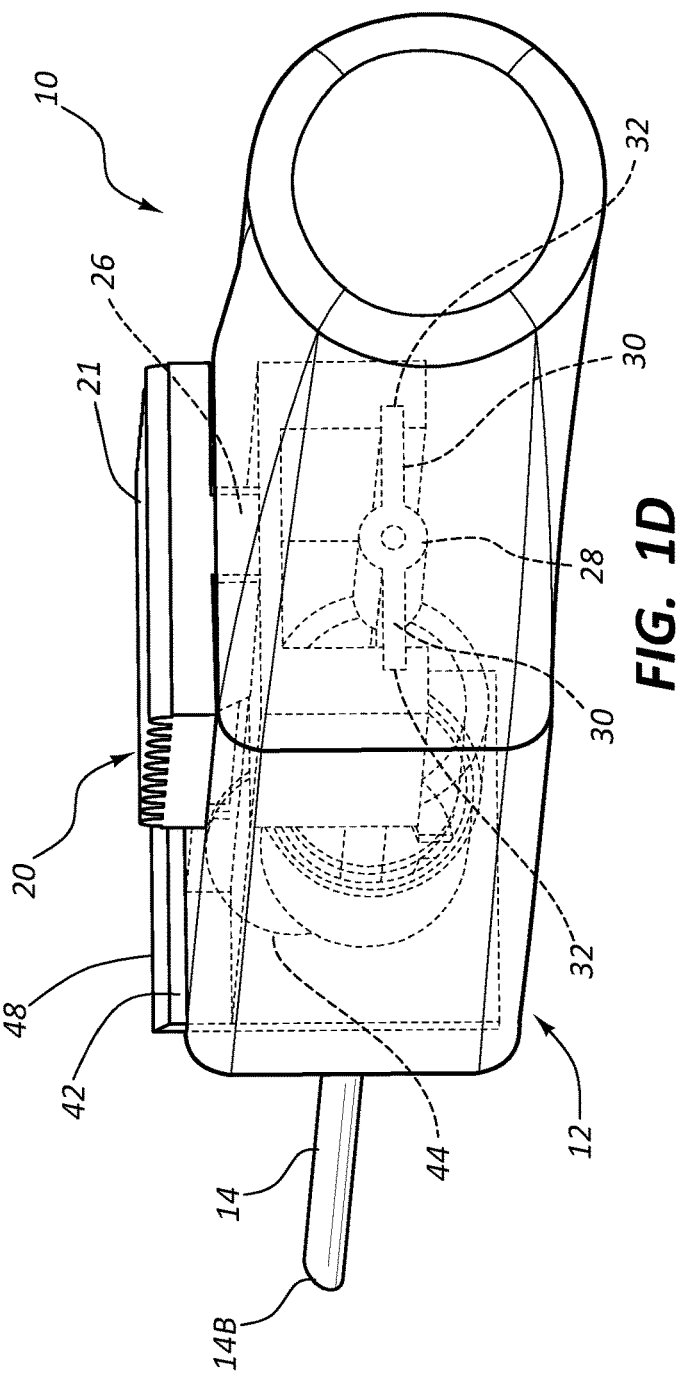

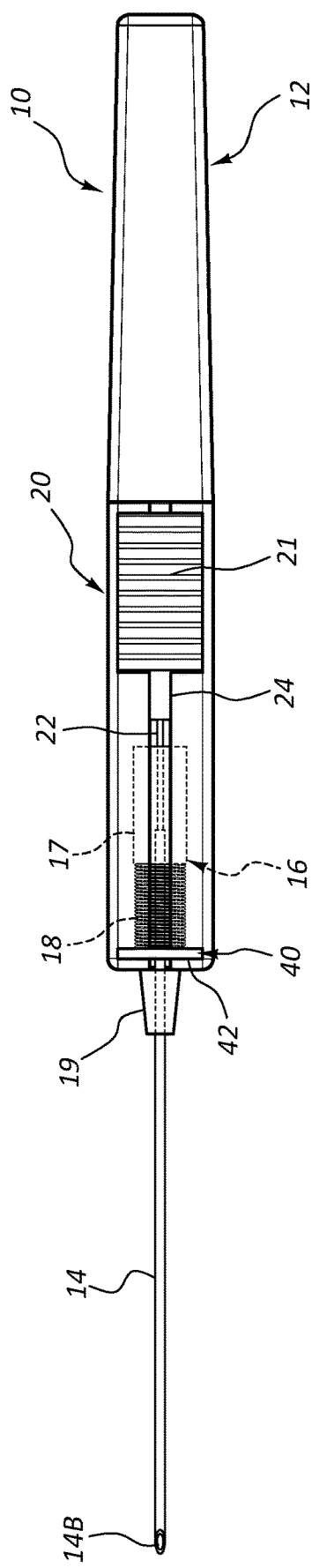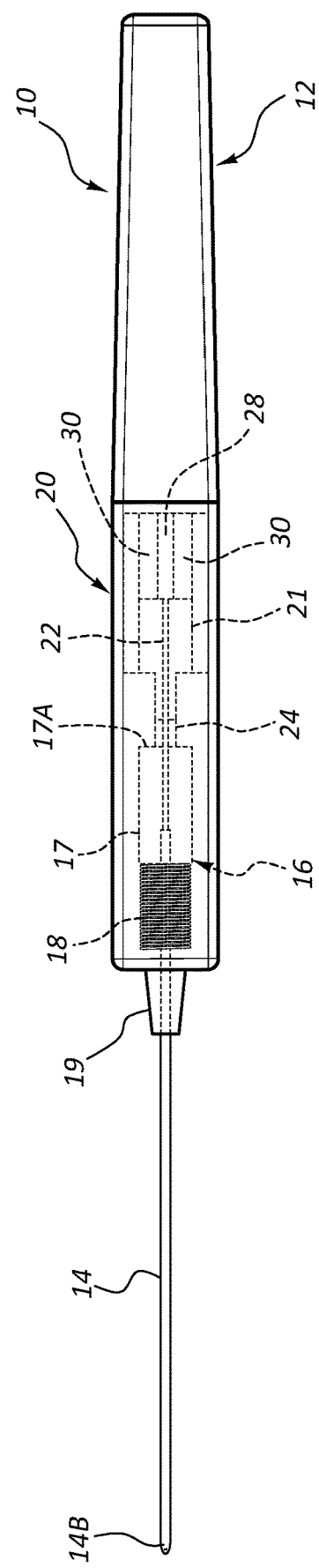
FIG. 1E
FIG. 1F

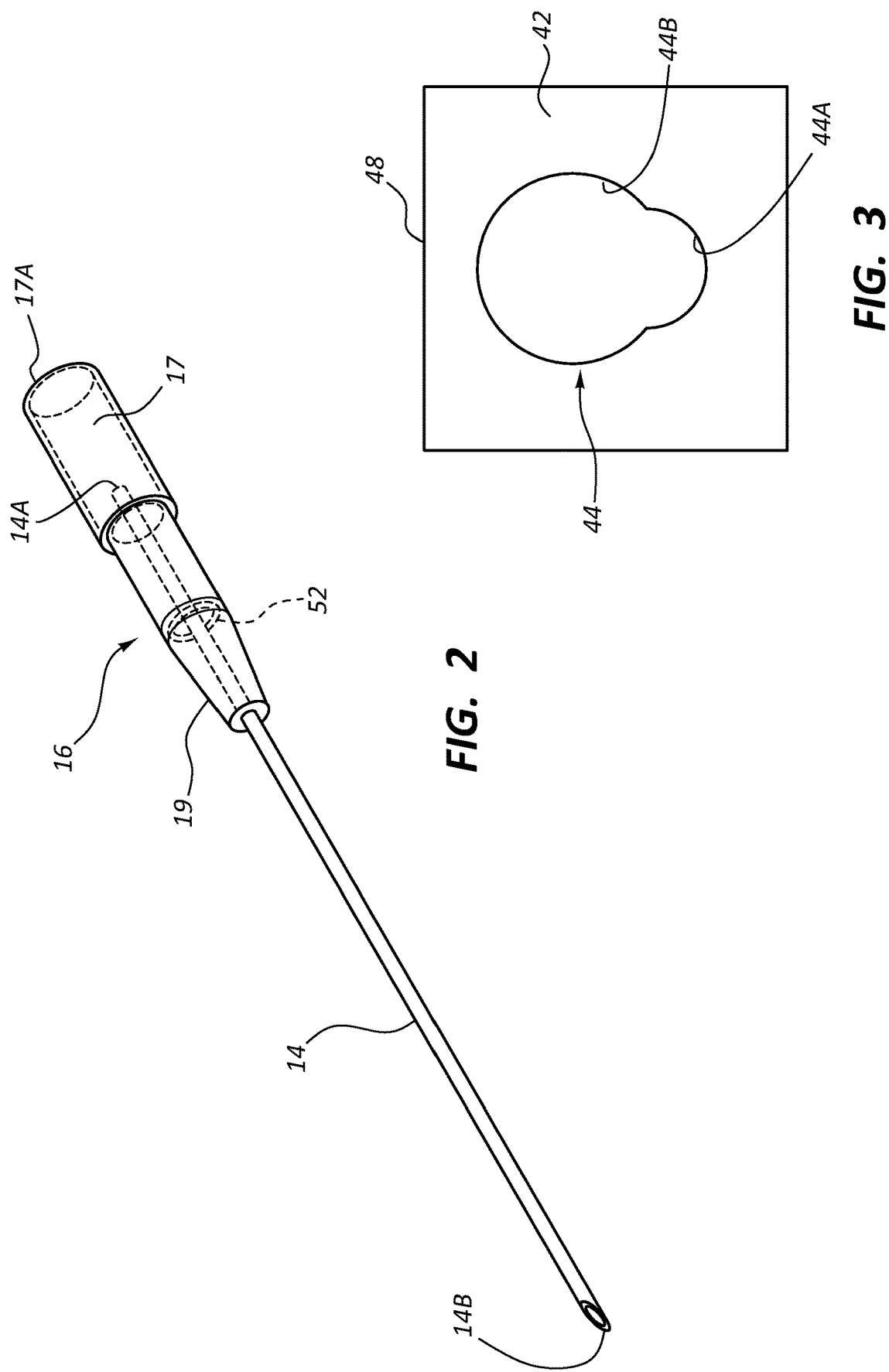

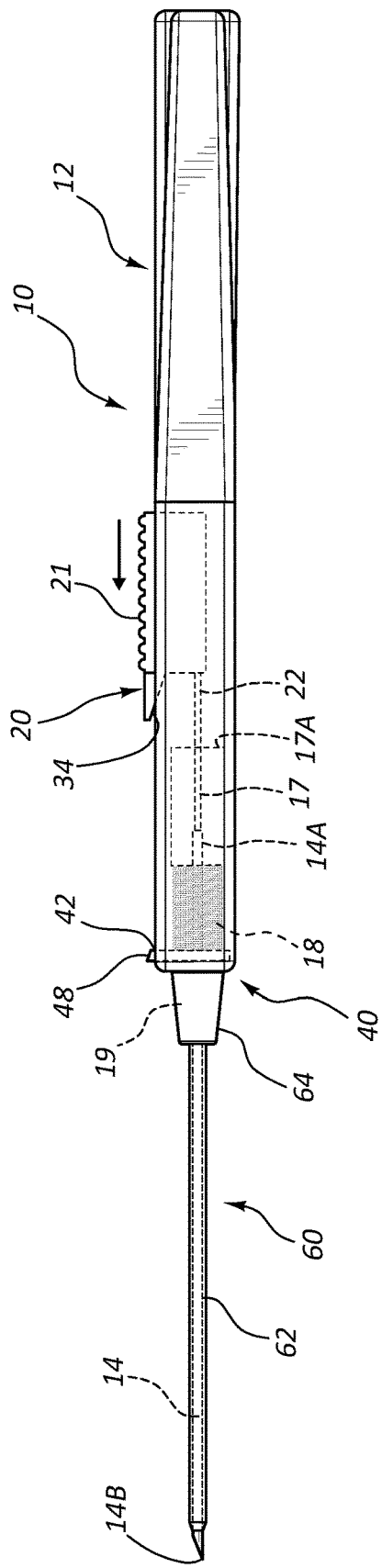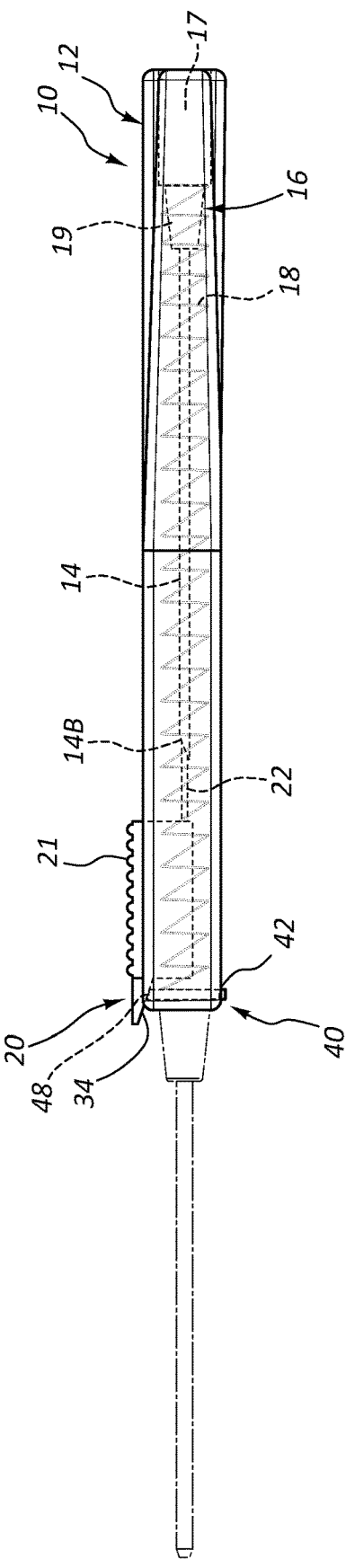
FIG. 4A
FIG. 4B

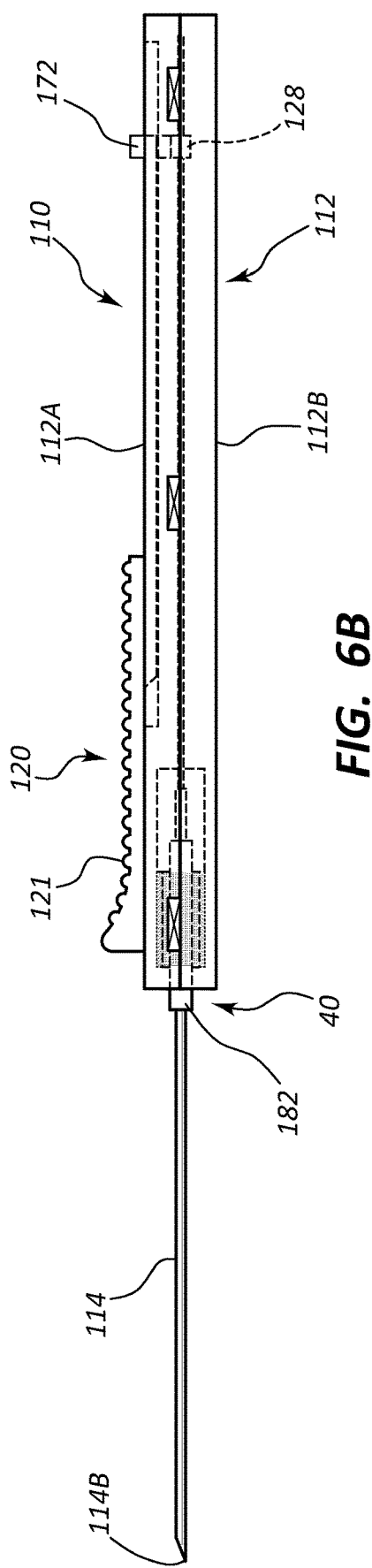
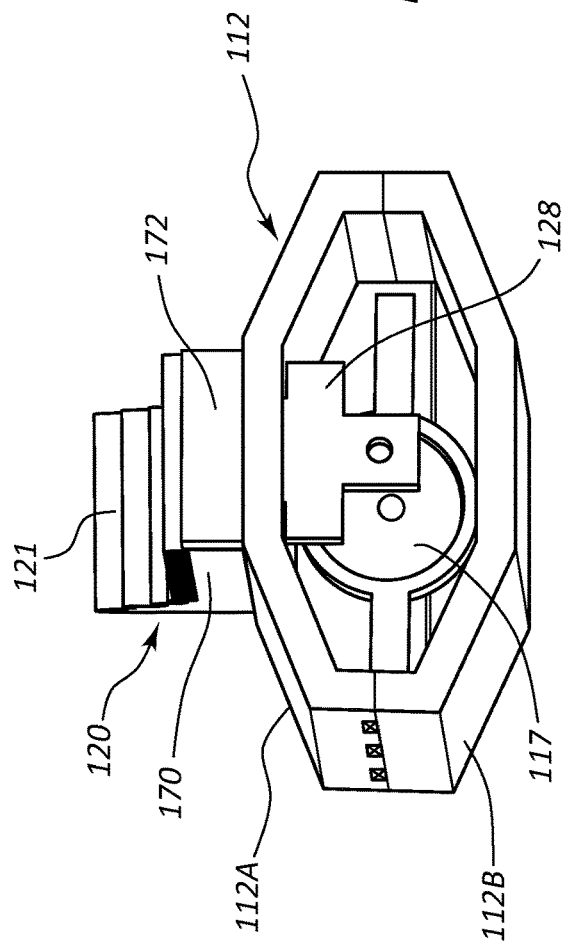

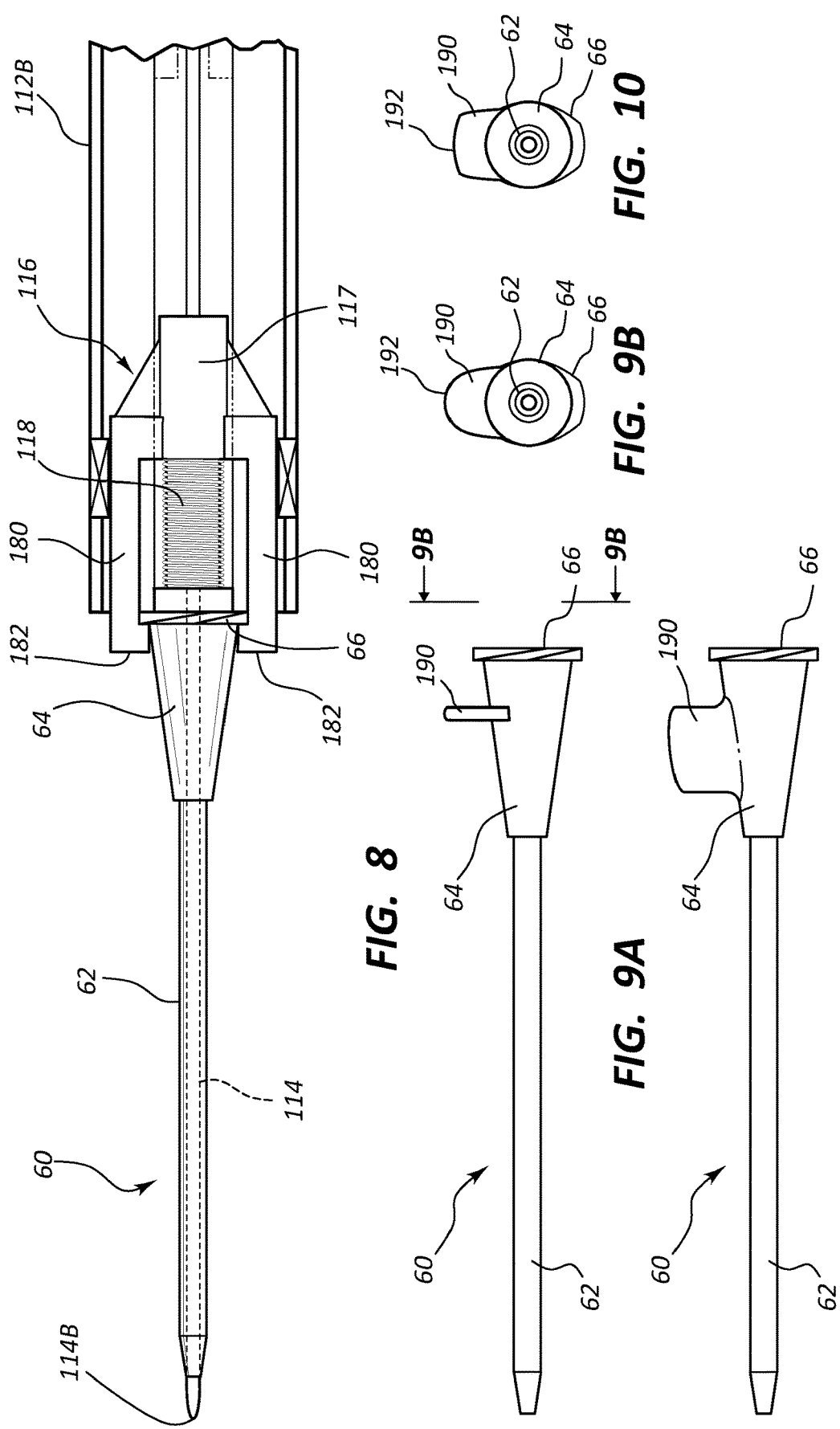

CATHETER INSERTION DEVICE INCLUDING RETRACTABLE NEEDLE

CROSS-REFERENCE TO RELATED APPLICATIONS

This application is a continuation of U.S. patent application Ser. No. 16/295,906, filed Mar. 7, 2019, now U.S. Pat. No. 11,033,719, which is a continuation of U.S. patent application Ser. No. 14/846,387, filed Sep. 4, 2015, now U.S. Pat. No. 10,232,146, which claims the benefit of U.S. Provisional Patent Application No. 62/046,722, filed Sep. 5, 2014, and titled "Guidewire-Assisted Catheter Insertion Device," each of which is incorporated by reference in its entirety into this application.

BRIEF SUMMARY

Briefly summarized, embodiments of the present invention are directed to a catheter insertion device for inserting a peripheral IV ("PIV") or other suitable catheter into a body of a patient. The catheter insertion device includes a retractable needle for establishing access to a subcutaneous vessel of the patient and a manually extensible guidewire for guiding the catheter, initially attached to the catheter insertion device, into the vessel. In one embodiment, one-handed operation of the device is possible.

In one embodiment, therefore, the catheter insertion device comprises a housing, a hollow needle retractably extending from the housing, a catheter initially disposed on a portion of the needle, a guidewire including a portion initially disposed within the needle, a guidewire advancement feature configured to selectively advance a distal end of the guidewire distally past a distal end of the needle, and a needle retention component configured to selectively enable retraction of the needle into the housing. The needle retention component is configured to be actuated by the guidewire advancement feature.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1F show various views of a catheter insertion device according to one embodiment;

FIG. 2 is a perspective view of a needle hub assembly of the catheter insertion device of FIGS. 1A-1F;

FIG. 3 is a side view of a plate of the catheter insertion device of FIGS. 1A-1F;

FIGS. 4A and 4B are side views of the catheter insertion device of FIGS. 1A-1F;

FIGS. 6A-6E shows various views of a catheter insertion device according to one embodiment;

FIG. 8 is a top cutaway view of the catheter insertion device of FIGS. 6A-6E;

FIGS. 9A and 9B are various views of a catheter assembly according to one embodiment;

FIG. 10 is an end view of a catheter assembly according to one embodiment; and

FIG. 11 is a side view of a catheter assembly according to one embodiment.

DETAILED DESCRIPTION OF SELECTED EMBODIMENTS

Figure 1A:
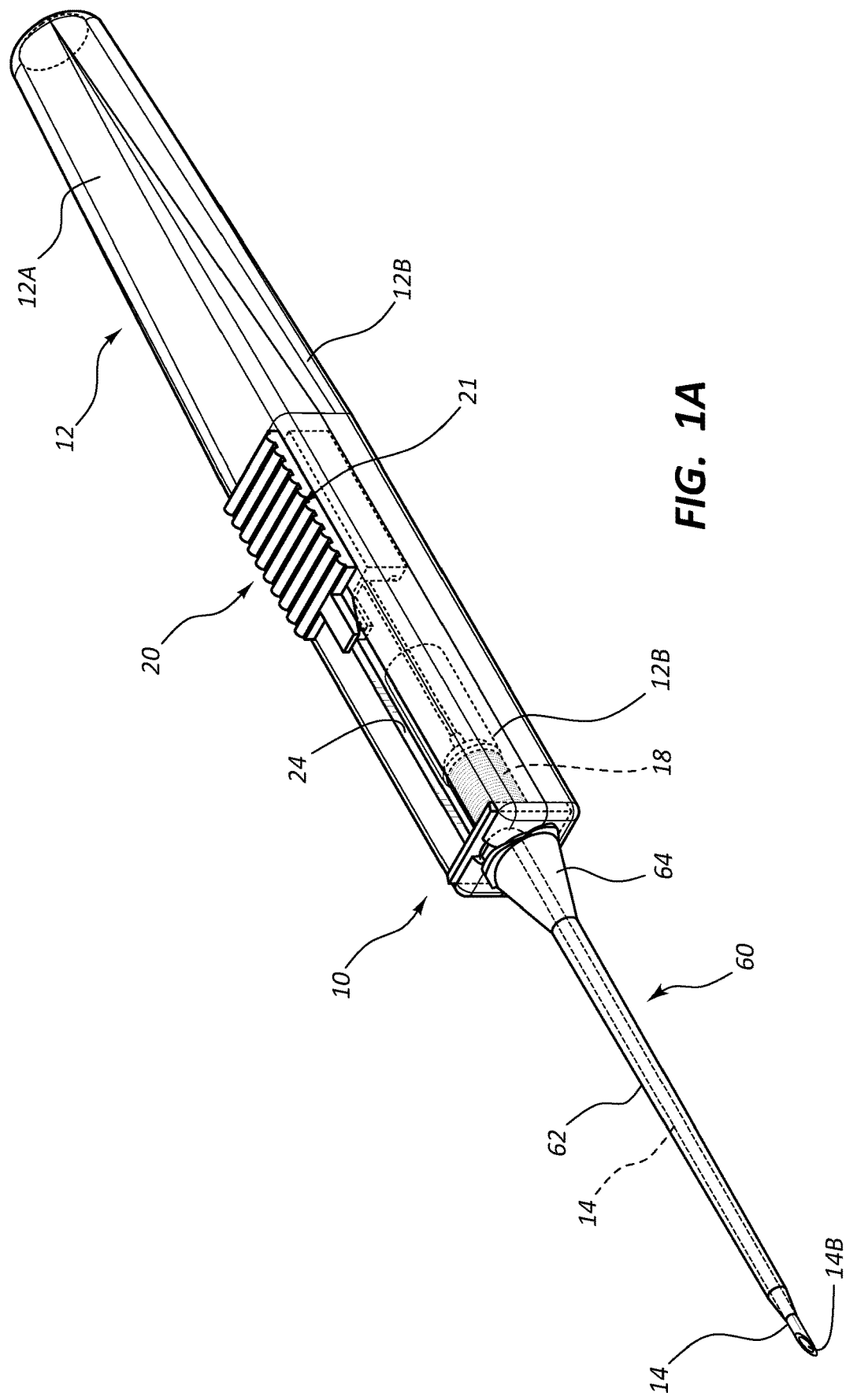

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a catheter insertion device for inserting a peripheral IV ("PIV") or other suitable catheter into a body of a patient. The catheter insertion device includes a retractable needle for establishing access to a subcutaneous vessel of the patient, for instance, and a manually extensible guidewire for guiding the catheter, initially attached to the catheter insertion device, into the vessel. In one embodiment, one-handed operation of the device is possible.

FIGS. 1A-1F depict various views of a catheter insertion device ("device") 10 according to one embodiment. As shown, the device 10 includes a housing 12 defined by a top housing portion 12A and a bottom housing portion 12B, though it is appreciated that the housing can be integrally formed as a single piece or include more than two portions, in other embodiments.

A hollow needle 14 initially and distally extends from a distal portion of the housing 12 and includes a distal end 14B that is configured to establish an insertion site for a catheter through the skin and vessel of the patient, in the present embodiment. A needle hub 16 is disposed in the housing 12 and secures the needle. A flash chamber 17 is included in the needle hub 16 and a proximal end 14A of the needle 14 is disposed therein so as to allow blood to enter the flash chamber when needle access to a vessel of the patient is established. The flash chamber 17 and adjacent portions of the housing 12 are translucent in one embodiment to enable clinician observation of blood when present in the flash chamber.

FIG. 2 gives additional details of the needle hub 16. As shown, the needle hub 16 further includes a distal, conical nose portion 19 that initially extends from the distal end of the housing 12 (FIG. 1C). A reduced-diameter neck 52 is included between the nose portion 19 and a more proximal, cylindrical portion of the needle hub 16.

A spring 18 is interposed between the flash chamber 17 and a distal portion of the housing 12 to enable selective retraction of the needle 14 fully into the housing so as to prevent accidental needle sticks after use of the device 10. Note that the size, type, position, and orientation of the spring is but one of various possible spring configurations. In addition, other resilient features or retraction mechanisms can be employed to selectively retract the needle into the housing.

A catheter assembly 60, including an elongate catheter tube 62 defining one or more lumens and a hub 64, is initially disposed over the needle 14 such that needle is received into the lumen of the catheter tube, as shown in FIG. 1A. Note that the catheter assembly 60 has been removed from various of the figures to be discussed herein, for clarity.

The device 10 in the present embodiment includes a guidewire advancement assembly for selectively advancing a guidewire 22 that is initially disposed both within the housing 12 and within a lumen defined by the hollow needle 14. As best seen in FIG. 1F, a proximal end of the guidewire 22 is attached to a guidewire hub 28 such that the guidewire extends distally into the flash chamber 17, through the proximal end 14A of the hollow needle 14, and into the lumen defined by the needle. The guidewire hub 28 includes two fins 30 that extend in opposite directions from one another and are configured to be slidably received in corresponding tracks 32 that are defined in a guidewire advancement handle 20, best seen in FIGS. 1C and 1D. The arrangement of the fins 30 and tracks 32 enable the guidewire hub 28 to separate from the guidewire advancement handle 20, as will be described further below.

In greater detail, the guidewire advancement handle 20 is slidably attached to the housing 12 so as to selectively advance or retract the guidewire 22. The guidewire advancement handle 20 includes a rail 26 that is disposed in a slot 24 of the top portion 12A of the housing 12 so as to enable the guidewire advancement handle to slide proximally and distally along the slot. A finger pad 21 is included on the guidewire advancement handle 20 to enable a user of the device 10 to selectively slide the guidewire advancement handle. Note that the size, shape, position, and configuration of the guidewire advancement handle 20 and finger pad 21 can vary from what is explicitly shown and described herein.

So configured, distal advancement of the guidewire 22 is accomplished by a user placing a finger on the finger pad 21 of the guidewire advancement handle 20 and sliding it from an initial proximal position to a more distal position with respect to the housing 12. This distal advancement of the guidewire advancement handle 20 also advances both the guidewire hub 28, which is removably attached to the guidewire advancement handle via the tracks 32 that receive the guidewire hub fins 30, as already described, and the guidewire 22 itself such that a distal portion thereof extends out of and distally past the distal end 14B of the needle 14. Note that other guidewire advancement handle and finger pad designs and configurations are possible in addition to those described herein.

A needle retention assembly is also included and in the present embodiment includes a needle retention component 40 to selectively enable retraction of the needle 14 into the housing after use of the device 10 so as to protect the user from an accidental needle stick. In the present embodiment, the needle retention component 40 includes a plate 42 that is movably disposed in a slot 46 defined at the distal end of the housing 12, as seen in FIGS. 1B-1F.

Figure 1B:
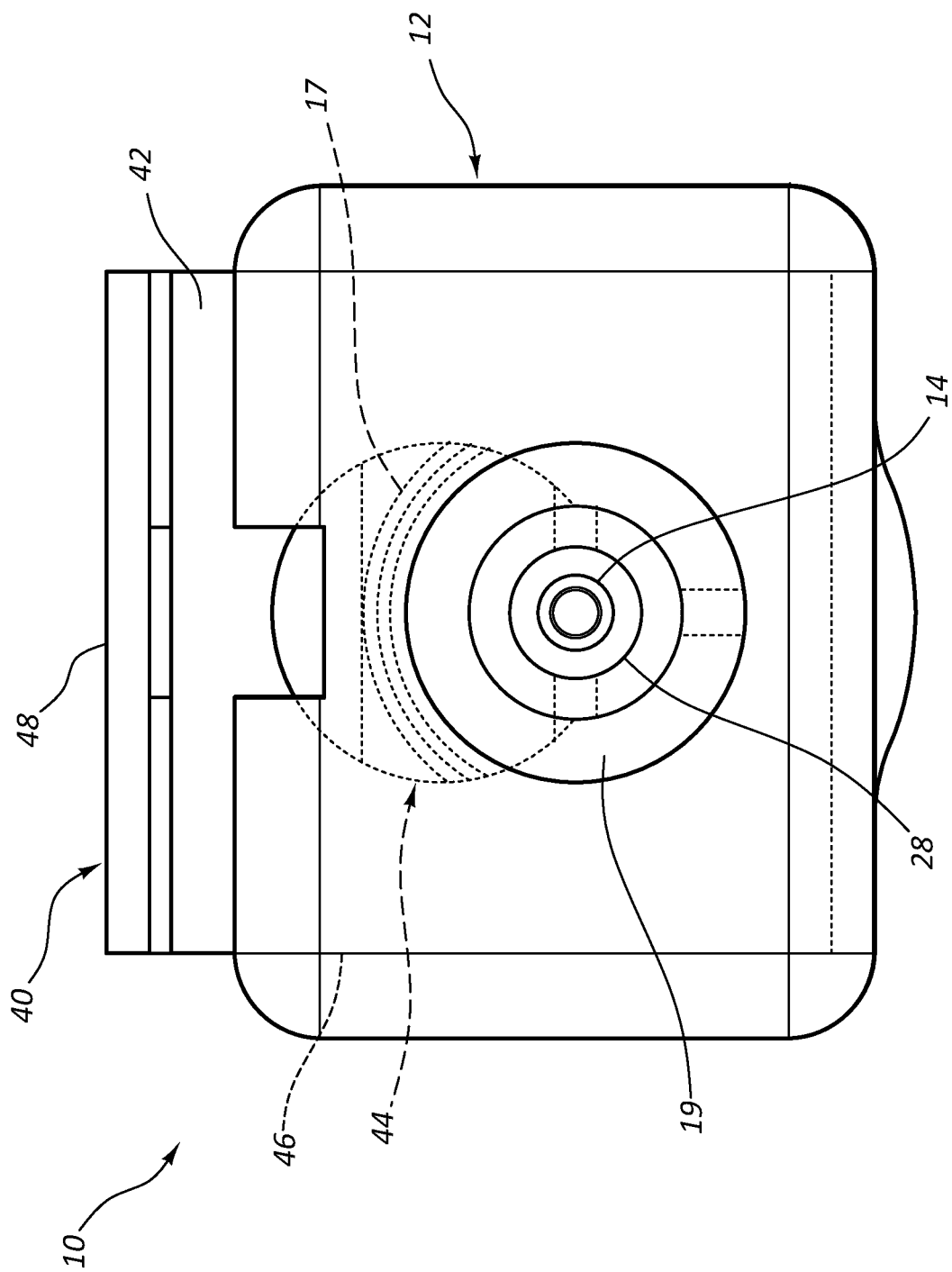

In greater detail and as seen in FIG. 3, the plate 42 defines a keyhole 44 that includes a semicircular portion 44A and a circular portion 44B, as shown. As seen in FIG. 1B, the plate 42 is initially placed in the slot 46 of the housing 12 in an un-depressed position such that the needle hub 16 extends through the keyhole 44. Specifically, the semicircular portion 44A of the keyhole 44 receives the neck 52 of the needle hub 16 such that the needle hub seats in the keyhole. Note that, in one embodiment, a spring or other component can be employed to maintain the plate 42 in the un-depressed position shown in FIG. 1B.

The plate 42 further includes an angled surface 48 (also referred to herein as a second angled surface) on a top edge thereof such that the angled face faces proximally. The angled surface 48 is configured to interact with a distally-facing angled surface 34 (also referred to herein as a first angled surface) disposed on the distal end of the guidewire advancement handle 20 when the guidewire advancement handle is distally advanced to distally extend the guidewire 22 out the distal end 14B of the needle 14, as will be further detailed below. Note that the angle, direction, shape, and other configuration of the first and second angled faces can vary from what is shown and described herein. For instance, in one embodiment the direction of the angled faces could be reversed from what is shown here. In another embodiment, the first and second angled surfaces can be replaced with engagement surfaces that interact to cause retraction of the needle into the housing.

The selective retraction of the needle 14 via actuation of the needle retention assembly described above is described here in connection with use of the device 10 to insert a catheter or other suitable tubular device the body of a patient, according to one embodiment and as depicted in FIGS. 4A and 4B. During operation, the needle 14 is first used to pierce through an insertion site on the skin surface of the patient and extend the distal end 14B of the needle into a subcutaneous vessel (or other intended destination). The guidewire advancement handle 20 is then slid distally from its proximal position with respect to the housing 12 so as to extend the guidewire 22 out the open distal end of the needle 14 and into the vessel. The guidewire 22 distally advances in this manner until the guidewire hub 28 contacts a proximal end 17A of the flash chamber 17, which ceases further distal guidewire movement. This is generally shown in FIG. 4A. The catheter assembly 60 can then be manually and distally advanced from the device 10 and inserted into the vessel, guided by the needle 14 and the guidewire 22.

Figure 5:
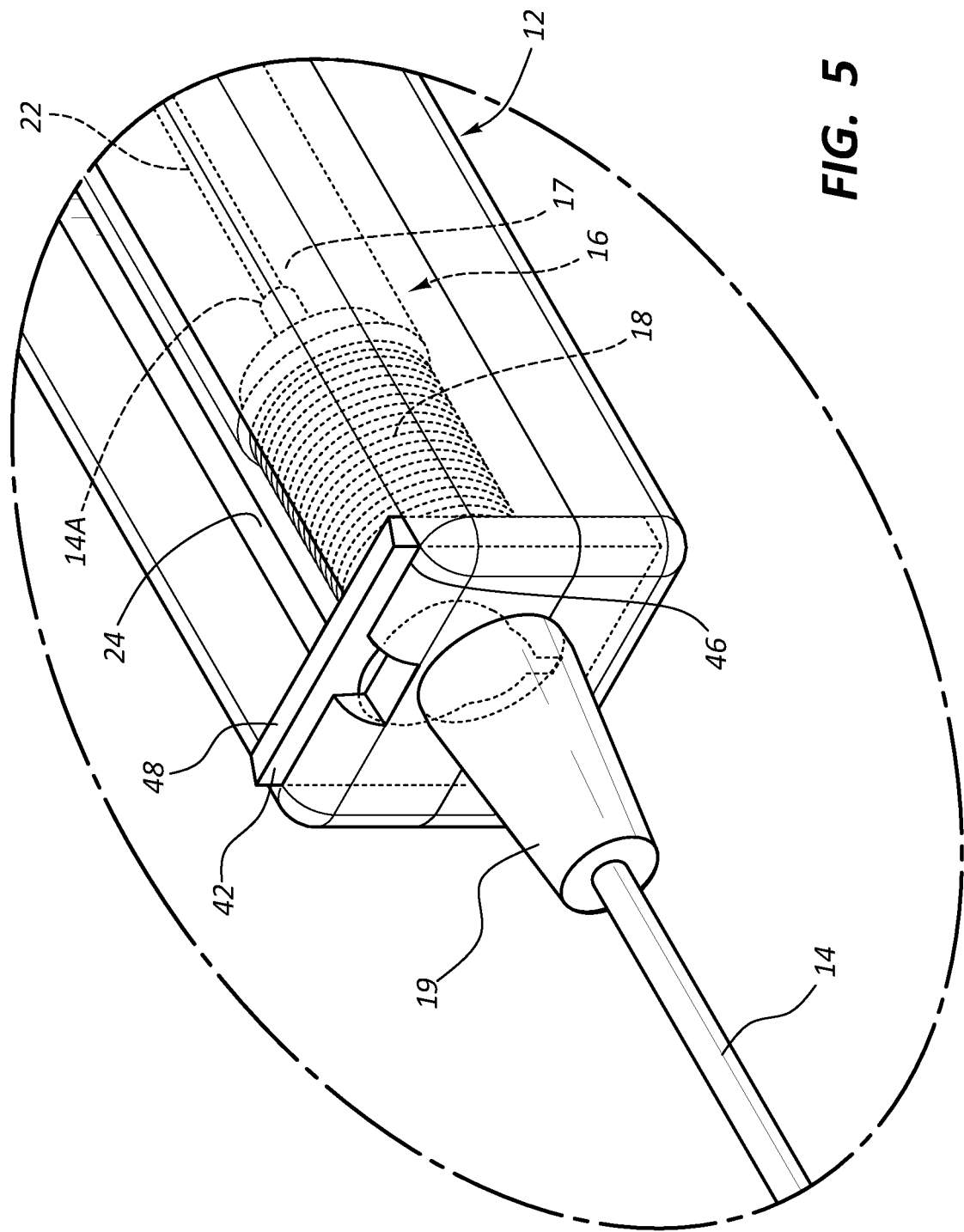
FIG. 5 is a perspective view of a distal portion of the catheter insertion device of FIGS. 1A-1F.

The device 10 can then be retracted away from the patient. At this time, the guidewire advancement handle 20 is slid further distally along the slot 24 in the top housing portion 12A. As the guidewire advancement handle 20 slides distally, the guidewire hub 28—abutting the proximal end 17A of the flash chamber 17 as described above—separates from the guidewire advancement handle via its fins 30 sliding out of the tracks 32 (FIG. 1D) as the guidewire advancement handle distally advances. The guidewire advancement handle 20 continues to slide distally until its first angled surface 34 engages and pushes down on the second angled surface 48 of the plate 42—the needle retention component 40 of the present embodiment. This causes the plate 42 to move from the un-depressed position shown in FIGS. 1B, 4A, and 5 to the depressed position shown in FIG. 4B. In turn, this causes the neck 52 of the needle hub 16 to unseat from the semicircular portion 44A of the plate keyhole 44 and to align with the circular portion 44A thereof.

No longer constrained by the plate 42, the needle hub 16 can now retract proximally within the housing, urged by the force of the spring 18, which can now expand from a compressed state (FIG. 5) to an expanded state (FIG. 4B). Retraction of the needle hub 16 causes the corresponding retraction of the needle 14 into the housing 12 until the distal end 14B thereof is disposed within the housing so as to prevent accidental needle sticks to the user. The proximal retraction of the needle hub 16 and connected flash chamber 17 correspondingly causes the guidewire hub 28 to also retract, given its abutment against the proximal end 17A of the flash chamber. This will correspondingly cause retraction of the guidewire 22 a predetermined amount. In one embodiment, the guidewire can be fully retracted into the housing. The now-placed catheter assembly 60 can then be dressed and the device 10 disposed of or otherwise safely handled.

In one embodiment, it is appreciated that detents or other features can be used to provide an aural and/or tactile cue when the guidewire advancement handle has advanced the guidewire to its full distal distance, when the guidewire advancement handle itself has advanced its full distal distance, and/or when other points along the travel path have been reached by the guidewire advancement handle. It is further appreciated that the device 10 of the present embodiment can be operated by only one hand of the user, thus facilitating ease-of-use.

FIGS. 6A-6E depict various views of the catheter insertion device ("device") 10 according to another embodiment. As shown, the device 10 includes a housing 112 defined by a top housing portion 112A and a bottom housing portion 112B, though it is appreciated that the housing can be integrally formed as a single piece or include more than two portions, in other embodiments.

A hollow needle 114 initially and distally extends from a distal portion of the housing 112 and includes a distal end 114B that is configured to establish an insertion site for a catheter through the skin and vessel of the patient, in the present embodiment. A needle hub 116 is disposed in the housing 112 and secures the needle. A flash chamber 117 is included in the needle hub 116 and a proximal end 114A of the needle 114 is disposed therein so as to allow blood to enter the flash chamber when needle access to a vessel of the patient is established. As before, the flash chamber and adjacent portions of the housing 112 are translucent in one embodiment to enable clinician observation of blood when present in the flash chamber.

A spring 118 is interposed between the flash chamber 117 and a distal portion of the housing 112 to enable selective retraction of the needle 114 fully into the housing so as to prevent accidental needle sticks after use of the device 10. Note that the size, type, position, and orientation of the spring is but one of various possible spring configurations. In addition, other resilient features or retraction mechanisms can be employed to selectively retract the needle into the housing.

Figure 6A:
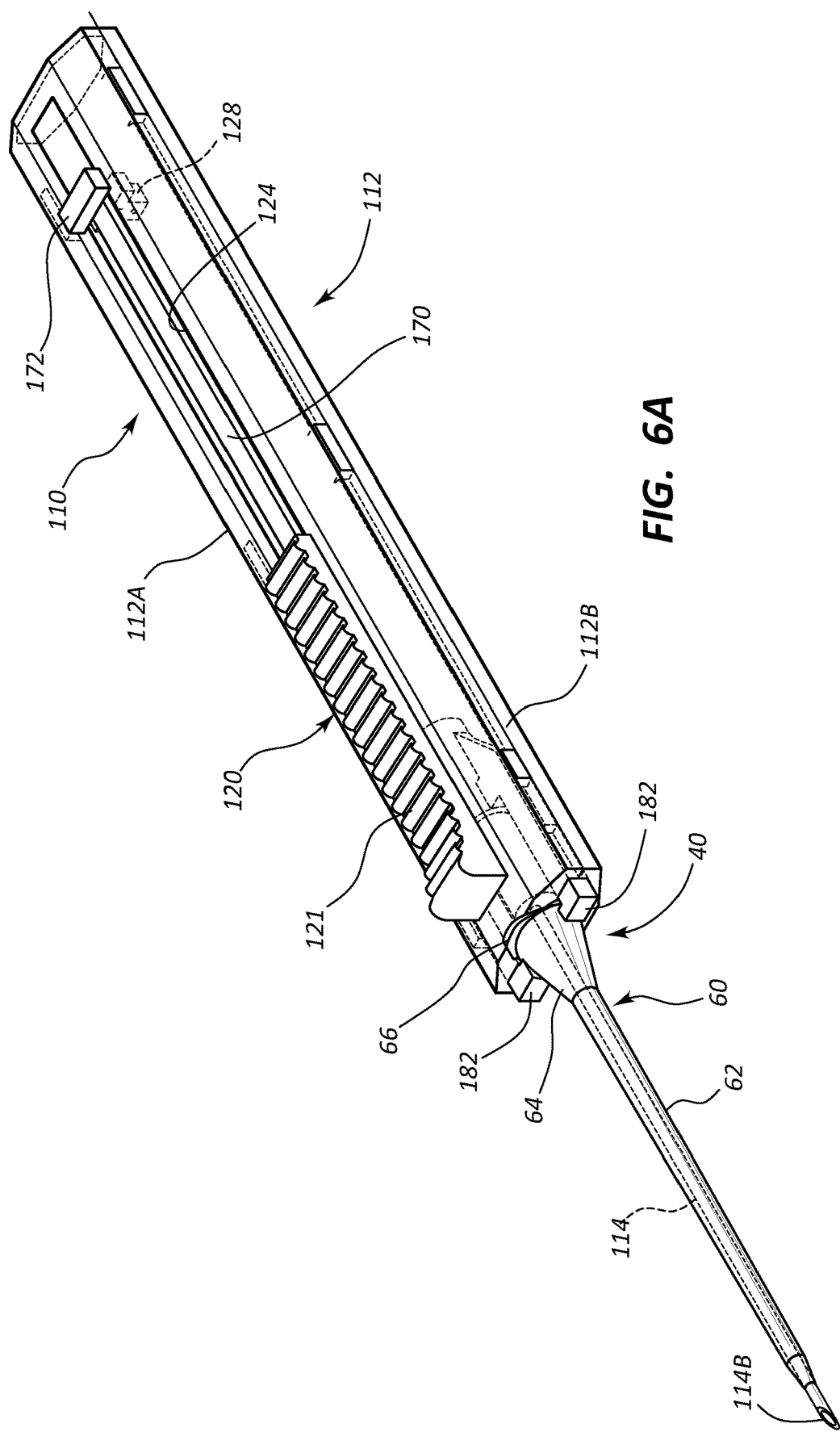
Figure 6D:
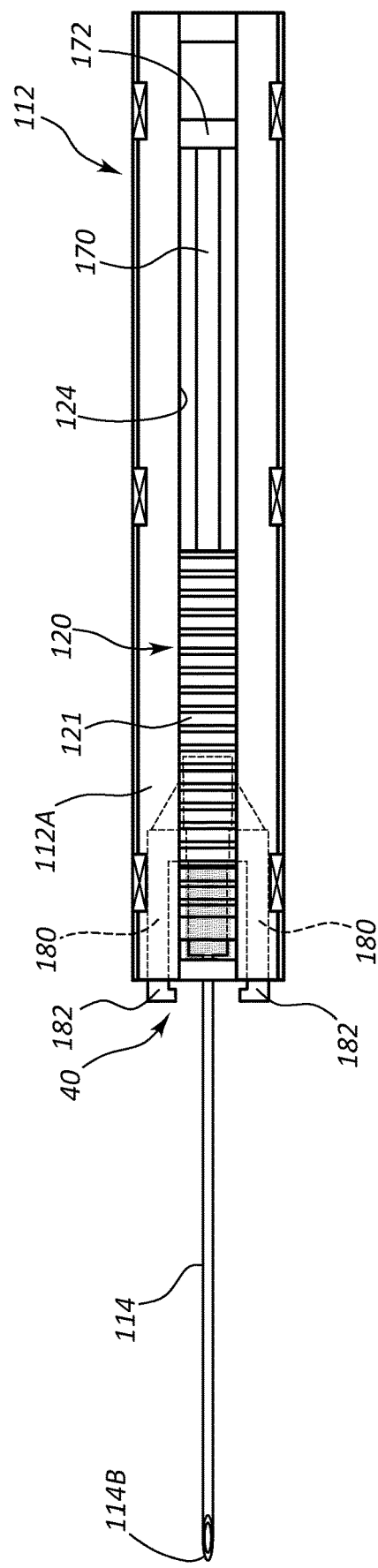
Figure 6E:
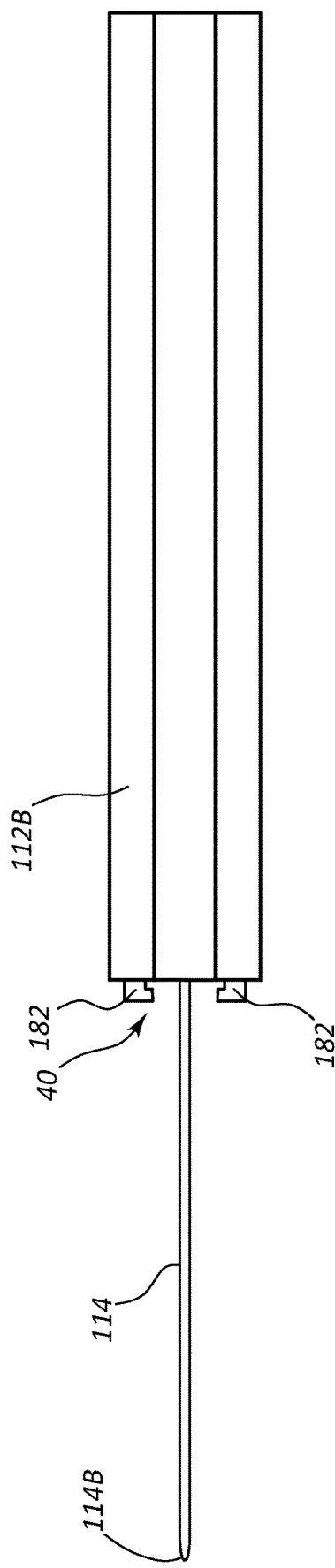

The catheter assembly 60, including the elongate catheter tube 62 and the hub 64, is initially disposed over the needle 114 such that needle is received into the lumen of the catheter tube, as shown in FIG. 6A. The catheter assembly 60 is removably attached to the device 10 in a manner to be described further below. Note that the catheter assembly 60 has been removed from various of the figures to be discussed herein, for clarity.

Figure 7A:
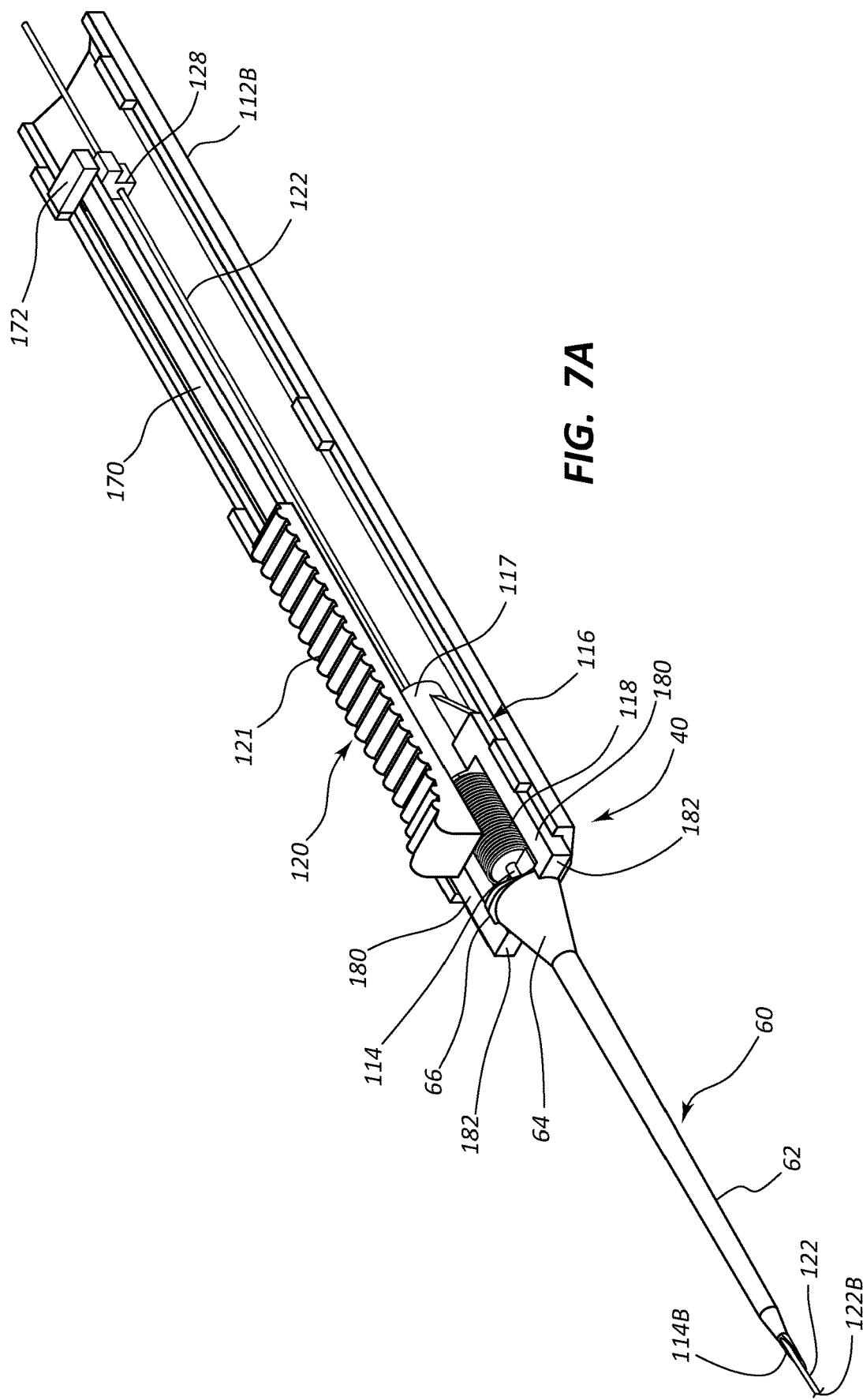
FIGS. 7A and 7B are various cutaway views of the catheter insertion device of FIGS. 6A-6E.

The device 10 in the present embodiment includes a guidewire advancement assembly for selectively advancing a guidewire 122 that initially extends from within the housing 12 and into a lumen defined by the hollow needle 114. As best seen in FIGS. 6C and 7A, a proximal end of the guidewire 122 is attached to a guidewire hub 128 such that the guidewire extends distally into the flash chamber 117 and through the proximal end 114A of the needle 114 and into the lumen define by the hollow needle.

The guidewire hub 128 is attached to a guidewire advancement handle 120, best seen in FIGS. 6A and 7A. In greater detail, the guidewire advancement handle 120 is slidably attached to the housing 112 via a slot 124 defined in the top housing portion 112A so as to selectively advance or retract the guidewire 122 when the guidewire advancement handle is slid distally or proximally, respectively, along the slot. A finger pad 121 is included on the guidewire advancement handle 120 to enable a user of the device 10 to selectively slide the guidewire advancement handle. As shown, the guidewire advancement handle includes an elongate body 170 that includes on its proximal end a raised portion 172, configured here as a block that assists in preventing the elongate body from falling through the slot 124. The guidewire hub 128 is also disposed on a proximal portion of the guidewire advancement handle body 170 so as to be disposed within the housing 112, as best seen in FIG. 6C. Note that the size, shape, position, and configuration of the guidewire advancement handle and finger pad can vary from what is explicitly shown and described herein.

So configured, distal advancement of the guidewire 122 is accomplished by a user placing a finger on the finger pad 121 of the guidewire advancement handle 120 and sliding it from an initial proximal position to a more distal position with respect to the housing 112. This distal advancement of the guidewire advancement handle 120 also advances both the guidewire hub 28, which is attached to the guidewire advancement handle body 170, and the guidewire 122 itself such that a distal end 122B thereof extends out of and distally past the distal end 114B of the needle 114. Note that other guidewire advancement handle and finger pad designs and configurations are possible in addition to those described herein.

A needle retention assembly is also included and in the present embodiment includes a needle retention component 40 to selectively enable retraction of the needle 114 into the housing after use of the device 10 so as to protect the user from an accidental needle stick. In the present embodiment, the needle retention component 40 includes two retention arms 180 that extend radially outward and distally from the flash chamber 117 of the needle hub 116, as best seen in FIG. 8. The length of each of the retention arms 180 is such that they terminate distal to the distal end of the housing 112. A hook 182 is included on each retention arm 180. The hooks 182 are configured to engage with threads 66 included on the hub 64 of the catheter assembly 60 so as to retain the catheter assembly in engagement with the device 10 during the initial phases of the catheter insertion procedure. It is appreciated that the shape, size, and configuration of the retention arms and the manner of engagement with the catheter assembly and its hub can vary from what is shown and described herein.

Figure 7B:
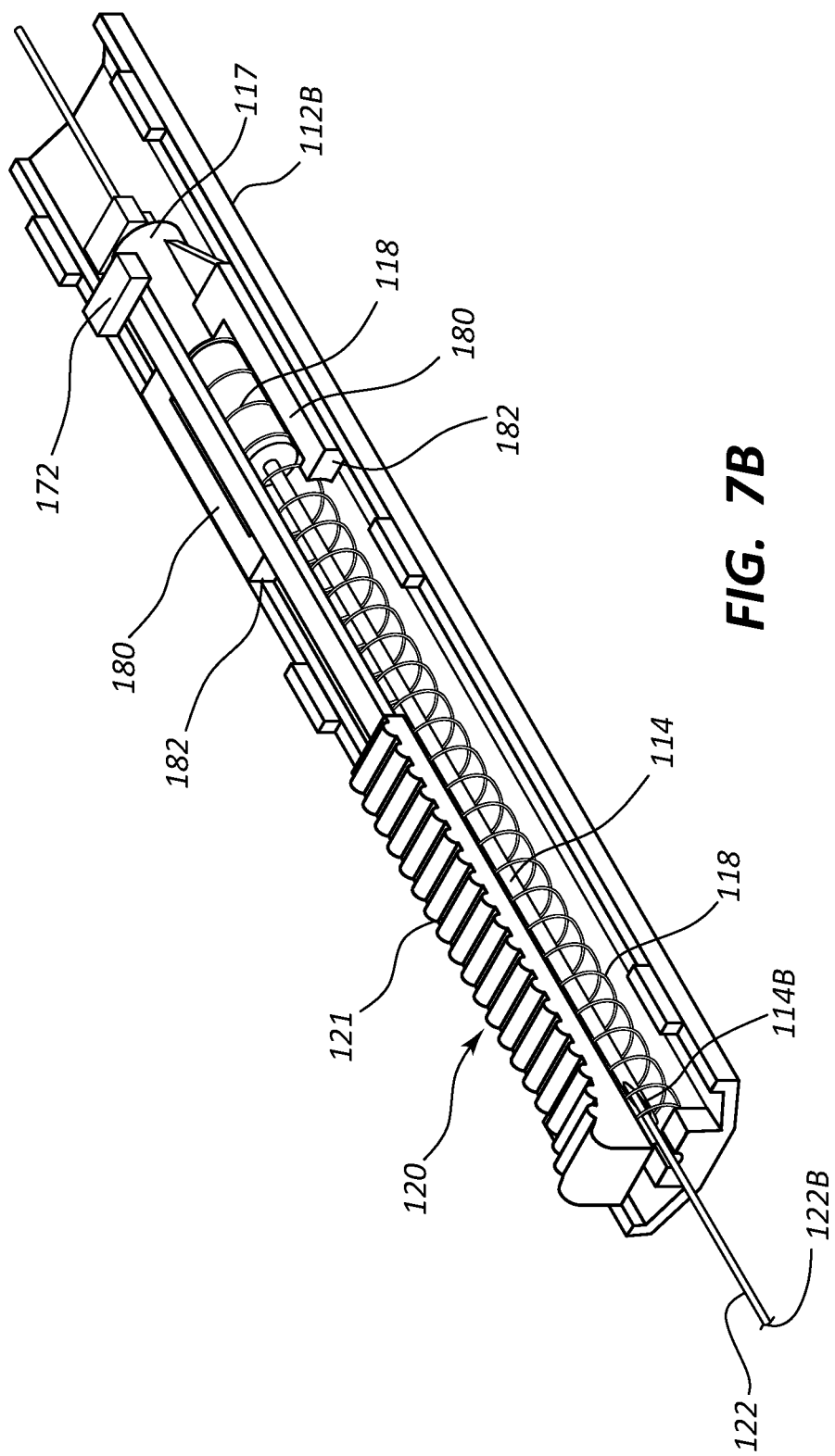

The selective retraction of the needle 114 via actuation of the needle retention assembly described above is described here in connection with use of the device 10 to insert a catheter or other suitable tubular device the body of a patient, according to one embodiment and as depicted in FIGS. 7A and 7B. During operation, the needle 114 is first used to pierce through an insertion site on the skin surface of the patient and extend the distal end 114B of the needle into a subcutaneous vessel (or other intended destination). The guidewire advancement handle 120 is then slid distally from its proximal position with respect to the housing 112 so as to extend the guidewire 122 out the open distal end of the needle 114 and into the vessel. The guidewire 122 distally advances in this manner until a distal portion of guidewire advancement handle 120 impinges on a distal portion of the housing 112 and/or the distal end of the slot 124. Note that, in other embodiments, a locking mechanism can be included so as to lock the guidewire advancement handle after distal advancement so as to prevent inadvertent movement thereof.

The catheter assembly 60 can then be manually removed from the device 10 and distally advanced from the device 10 and inserted into the vessel, guided by the needle 14 and the guidewire 22. The catheter is removed by the user by manually twisting the catheter hub 64 so as to release the threads 66 thereof from engagement with the hooks 182 of the retention arms 180. A finger tab 190 included on the catheter hub 64, seen in FIGS. 6A and 7A, can be employed to assist the user in twisting the catheter hub. The finger tab 190 can assist the user in twisting the catheter hub 64 with the same hand that is grasping the device 10, in one embodiment. Once released in this manner, the catheter tube 62 can be distally advanced into the vessel, as just described.

Engagement of the catheter hub threads 66 with the hooks 182 of the retention arms 180 prevents retraction of the retraction arms and, correspondingly, the needle hub 116 and attached needle 114. Upon detachment of the catheter assembly 60 from the retraction arms 180, as described above, the needle hub 116 can now retract proximally within the housing, urged by the force of the spring 118, which can now expand from a compressed state (FIG. 7A) to an expanded state (FIG. 7B). Retraction of the needle hub 116 causes the corresponding retraction of the needle 114 into the housing 112 until the distal end 114B thereof is disposed within the housing so as to prevent accidental needle sticks to the user.

Despite retraction of the needle 114, the guidewire 122 remains in its distally extended state within the vessel. The catheter assembly 60 is distally advanced into the vessel as desired, after which the device 10 can be withdrawn from the patient, which causes removal of the guidewire 122 from the vessel and insertion site. The catheter assembly 60 can be dressed as needed and the device 10 disposed of or otherwise safely handled.

FIGS. 9A and 9B depict various details of the catheter assembly 60 for use with the catheter insertion device 10 described herein in connection with FIGS. 6A-8 or with other suitable catheter insertion devices. As shown, the catheter hub 64 includes the finger tab 190, described further above as a component to assist with twisting of the catheter hub by the user in order to separate the catheter assembly 60 from the device 10. As best seen in FIG. 9B, the finger tab 190 can include a profile 192, such as rounded, as shown here. Other profiles are also possible, including squared, as shown in FIG. 10, or elongated as shown in FIG. 11. Of course, various other finger tab profiles are also possible.

In light of the above, in one embodiment, a catheter insertion device, such as the devices 10 described herein, can be manufactured in one embodiment by providing a housing with a guidewire and a guidewire advancement feature, such as the guidewire advancement assemblies discussed herein, including the guidewire advancement handles 20, 120 and associated components. A needle is also provided so as to retractably extend from the housing, and a catheter assembly is removably disposed on the needle. A needle retention assembly is also included with the catheter insertion device, such as the needle retention component 40 described above, for enabling selective retraction of the needle into the housing to prevent accidental needle sticks.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of inserting a catheter into a blood vessel, comprising:
    accessing a catheter insertion device comprising:
        a housing;
        a needle including a needle hub, a needle lumen, and a needle tip, the needle hub having a portion in the housing;
        a catheter coupled to a catheter hub, the catheter positioned over the needle such that the needle tip extends past a distal end of the catheter;
        a guidewire having a distal end;
        a guidewire handle coupled to the guidewire, the guidewire handle including a finger pad positioned on a surface of the housing; and
        a pair of retention arms that extend from the needle hub, wherein a distal portion of each of the pair of retention arms extends distally of the housing, the distal portion of each of the pair of retention arms engaging the catheter hub;
    inserting the needle tip and the distal end of the catheter into the blood vessel;
    sliding the finger pad from a first position, in which the distal end of the guidewire is disposed in the needle lumen, to a second position, in which the distal end of the guidewire extends past the needle tip;
    moving the catheter hub out of engagement with the pair of retention arms; and
    advancing the catheter over the guidewire into the blood vessel.

2. The method of inserting according to claim 1, wherein the catheter insertion device further comprises a spring in the housing, wherein moving the catheter hub out of engagement with the pair of retention arms permits the spring to retract the needle into the housing.

3. The method of inserting according to claim 2, wherein the catheter insertion device further comprises a flash chamber coupled to the needle hub, the flash chamber having a diameter greater than a diameter of the needle hub, wherein the spring is positioned over the needle hub in the housing, and wherein the spring is compressed between the flash chamber and the housing.

4. The method of inserting according to claim 1, wherein moving the catheter hub out of engagement with the pair of retention arms comprises rotating the catheter hub.

5. The method of inserting according to claim 4, wherein the catheter hub includes a finger tab to facilitate rotating the catheter hub.

6. The method of inserting according to claim 1, wherein each of the steps: accessing the catheter insertion device, inserting the needle tip and the distal end of the catheter into the blood vessel, sliding the finger pad from the first position to the second position, and sliding the finger pad from the second position to the third position, is performed using a single hand without removing the single hand from the catheter insertion device.

* * * * *